(12) United States Patent
Harms et al.

(10) Patent No.: US 9,078,970 B2
(45) Date of Patent: Jul. 14, 2015

(54) DRUG DELIVERY DEVICE AND METHOD OF MANUFACTURING A DRUG DELIVERY DEVICE

(75) Inventors: Michael Harms, Frankfurt am Main (DE); Steffen Raab, Frankfurt am Main (DE)

(73) Assignee: SANOFI-AVENTIS DEUTSCHLAND GMBH, Frankfurt am Main (DE)

( * ) Notice: Subject to any disclaimer, the term of this patent is extended or adjusted under 35 U.S.C. 154(b) by 410 days.

(21) Appl. No.: 13/440,203

(22) Filed: Apr. 5, 2012

(65) Prior Publication Data

US 2012/0191049 A1    Jul. 26, 2012

Related U.S. Application Data

(63) Continuation of application No. 13/123,530, filed as application No. PCT/EP2009/063075 on Oct. 8, 2009.

(30) Foreign Application Priority Data

Oct. 13, 2008    (EP) .................................... 08017889

(51) Int. Cl.
*A61M 5/00* (2006.01)
*A61M 5/24* (2006.01)
*A61M 5/315* (2006.01)

(52) U.S. Cl.
CPC .............. *A61M 5/24* (2013.01); *A61M 5/31585* (2013.01); *A61M 5/31543* (2013.01); *A61M 5/31595* (2013.01); *A61M 2005/2407* (2013.01); *A61M 2005/2477* (2013.01);

(Continued)

(58) Field of Classification Search
CPC .............. A61M 5/24; A61M 5/31585; A61M 2005/2407; A61M 2005/2477
USPC ......... 604/110–111, 117, 135–137, 156–157, 604/187, 192, 196–198
See application file for complete search history.

(56) References Cited

U.S. PATENT DOCUMENTS 3,742,948 A      7/1973   Post et al.
2001/0039394 A1* 11/2001  Weston ........................ 604/72

(Continued)

FOREIGN PATENT DOCUMENTS

DE      10 2004 053529    5/2006
WO         96/17640       6/1996

(Continued)

OTHER PUBLICATIONS

European Search Report for EP App. No. 12160352, completed Apr. 17, 2012.
International Search Report for corresponding PCT application No. PCT/EP2009/063075.

(Continued)

*Primary Examiner* — Aarti B Berdichevsky
(74) *Attorney, Agent, or Firm* — McDonnell Boehen Hulbert & Berghoff LLP

(57) ABSTRACT

The present invention relates to drug delivery device and a and method of manufacturing a drug delivery device with a housing having a proximal end and a distal end, a cartridge adapted to accommodate a drug, a cartridge retaining member adapted to retain the cartridge, the cartridge retaining member being secured to the housing, and a spring washer being arranged within the housing so as to exerting a force on the cartridge and securing the cartridge against movement with respect to the cartridge retaining member and against movement with respect to the housing.

18 Claims, 5 Drawing Sheets

(52) U.S. Cl.
CPC ... *A61M 2005/2488* (2013.01); *A61M 2207/00* (2013.01); *Y10T 29/49863* (2015.01)

(56) References Cited

U.S. PATENT DOCUMENTS

2005/0267422 A1* 12/2005 Kriesel .................... 604/288.01
2007/0021718 A1   1/2007 Burren et al.

FOREIGN PATENT DOCUMENTS

WO  2005/032449   4/2005
WO  2010/139635   12/2012

OTHER PUBLICATIONS

International Preliminary Report on Patentability for corresponding PCT application No. PCT/EP2009/063075.

* cited by examiner

DRUG DELIVERY DEVICE AND METHOD OF MANUFACTURING A DRUG DELIVERY DEVICE

CROSS REFERENCE TO RELATED APPLICATIONS

The present application is a continuation of U.S. patent application Ser. No. 13/123,530, filed Aug. 17, 2011, which is a U.S. National Phase Application pursuant to 35 U.S.C. §371 of International Application No. PCT/EP2009/063075 filed Oct. 8, 2009, which claims priority to European Patent Application No. 08017889.0 filed on Oct. 13, 2008. The entire disclosure content of these applications are herewith incorporated by reference into the present application.

TECHNICAL FIELD

The present invention relates to a drug delivery device and a method of manufacturing a drug delivery device. Drug delivery devices are used for the administration of a drug, for example insulin, heparin or growth hormones. Some devices are configured to deliver a plurality of doses. Additionally some devices are configured to allow setting of different dose sizes which are to be delivered. Here it is important that the size of the dose can be precisely set and the set dose can be reliably delivered.

BACKGROUND

In US 2007/0021718 A1 a syringe is shown having a spring which is arranged between a housing insert and a driving element. The spring may serve as compensation for longitudinal tolerances in order to support a medical container in an injection device.

In U.S. Pat. No. 3,742,948 a syringe is shown having a pressure member constructed as a cup spring. The pressure member includes resilient lugs which bear on the upper edge of the liquid container with their free end.

Further medication delivery devices are known from the documents WO 2005/032449 A1 and DE 10 2004 053529 A1.

It is an aim of the present invention to provide for an improved drug delivery device. In particular, a drug delivery device should be provided, which allows for improved operability with respect to dosage control and/or improved reproducibility of the dosage in connection with different cartridges.

SUMMARY

For this aim, a drug delivery device comprises a housing with a proximal end and a distal end, a cartridge adapted to accommodate a drug, a cartridge retaining member adapted to retain the cartridge, the cartridge retaining member being secured to the housing, and a spring washer being arranged within the housing so as to exert a force on the cartridge and secure the cartridge against movement with respect to the cartridge retaining member and, preferably, against movement with respect to the housing.

In a drug delivery device of this kind movement of the cartridge with respect to the housing and/or the cartridge retaining member is reduced or even avoided on account of the spring washer, which exerts the force on the cartridge. The spring washer can reduce play between cartridge and housing and/or between cartridge and cartridge retaining member. This is, for example, particularly advantageous when cartridges with different lengths are to be used in the drug delivery device. Thus, the drug delivery device may be a reusable device. Manufacturing tolerances in cartridge lengths can thus be compensated by means of the spring washer. Consequently, during operation of the drug delivery device, axial movement of the cartridge in the cartridge retaining member can be reduced or even prevented and dose accuracy can be increased. The spring washer allows securing the cartridge within the cartridge retaining member without requiring much space. Consequently a very compact drug delivery device can be formed.

In a further embodiment, the spring washer is arranged so as to abut the cartridge, preferably on a side of the cartridge that faces the proximal end of the housing.

The spring washer may keep the cartridge fixed in the cartridge retaining member by abutting the cartridge, preferably on a side of the cartridge that faces the proximal end of the housing. Accordingly, axial movement of the cartridge with respect to the cartridge retaining member is reduced or even prevented.

The spring washer may exert a force on the cartridge in the distal direction. The spring washer may be loaded or biased so as to exert the force on the cartridge.

In a further embodiment, the spring washer is fixed to the housing. In particular, the spring washer may be secured to the housing so as to prevent relative axial movement between spring washer and housing in that region in which the spring washer is secured to the housing.

According to this embodiment, the counter force when the spring washer exerts a force on the cartridge acts on the housing with the spring washer being held at its axial position.

In one embodiment, the drug delivery device comprises a piston rod for dispensing a dose of the drug from the device when the piston rod is driven in the distal direction and the spring washer comprises an opening, the opening being arranged so as to allow the piston rod to run through the opening.

In this example, the spring washer can easily be implemented together with conventional drug delivery mechanisms, which utilize a piston rod or the like. Accordingly, the manufacturability of the drug delivery device is facilitated as no significant design changes must be performed.

According to a further embodiment, the spring washer is curved in an axial and/or a radial direction. The axis may extend between the proximal end and the distal end of the housing.

Loading the spring washer and exerting a force on the cartridge is facilitated by shaping the spring washer in this way.

In a further embodiment, the spring washer is a Belleville type spring washer.

Spring washers of this kind can be easily implemented in the drug delivery device.

In one embodiment, the spring washer is fixed to a sleeve member of the housing, preferably a threaded sleeve member of the housing.

According to this embodiment, the spring washer may be implemented in a conventional housing of a drug delivery device, without performing significant design changes on the housing. The (threaded) sleeve member may simultaneously be used to secure the cartridge retaining member to the housing, e.g. by means of an inner thread.

In one embodiment, the drug delivery device comprises a further washer, the further washer preferably being arranged on the proximal side of the spring washer. The further washer is preferably arranged to be abutable by the spring washer.

In one embodiment, the further washer is arranged to limit the loading distance of the spring washer.

During insertion of the cartridge, a force in the proximal direction may be exerted on the spring washer, e.g. when (releasably) securing the cartridge retaining member with the cartridge being retained therein to the housing. In order to prevent the spring washer from being permanently plastically deformed, the further washer can be arranged on the proximal side of the spring washer. The further washer may limit the distance by which the spring washer may be deformed.

In one embodiment, the further washer is a disk washer or a spring washer. If the further washer is a spring washer, it preferably has a higher strength as compared to the spring washer that exerts the force on the cartridge. If the spring washer is loaded by a given force, the risk of overloading the spring washer, e.g. in the region of plastic deformation, can be reduced by providing a further spring washer of higher spring strength.

In one embodiment, the further washer is arranged to limit deformation of the spring washer to elastic deformation. In this example, the spring characteristics of the spring washer can be conserved as no plastic, i.e. non-elastic, deformation takes place.

According to a further embodiment, the further washer is curved in an axial and/or a radial direction. Preferably, the curvature of the further washer corresponds to or resembles the curvature of the spring washer.

In this example, the curvature of the further washer may be adapted to the curvature of spring washer in that region in which the further washer and the spring washer overlap as seen along the axial direction. This allows for a smooth abutment of the spring washer and the further washer.

For the above mentioned aim, a method of manufacturing a drug delivery device comprises the steps of: providing a housing with a proximal end and a distal end, providing a cartridge adapted to accommodate a drug, providing a cartridge retaining member adapted to retain the cartridge, arranging a spring washer within the housing and securing the cartridge retaining member to the housing, thereby loading the spring washer so as to exert a force on the cartridge and to secure the cartridge against displacement, in particular against axial displacement, with respect to the cartridge retaining member.

For the above mentioned aim, a spring washer is used to secure a cartridge which contains a drug in a cartridge retaining member of a drug delivery device against displacement, preferably against axial displacement, with respect to the cartridge retaining member.

Other features will become apparent from the following detailed description when considered in conjunction with the accompanying drawings.

DETAILED DESCRIPTION

Figure 1:
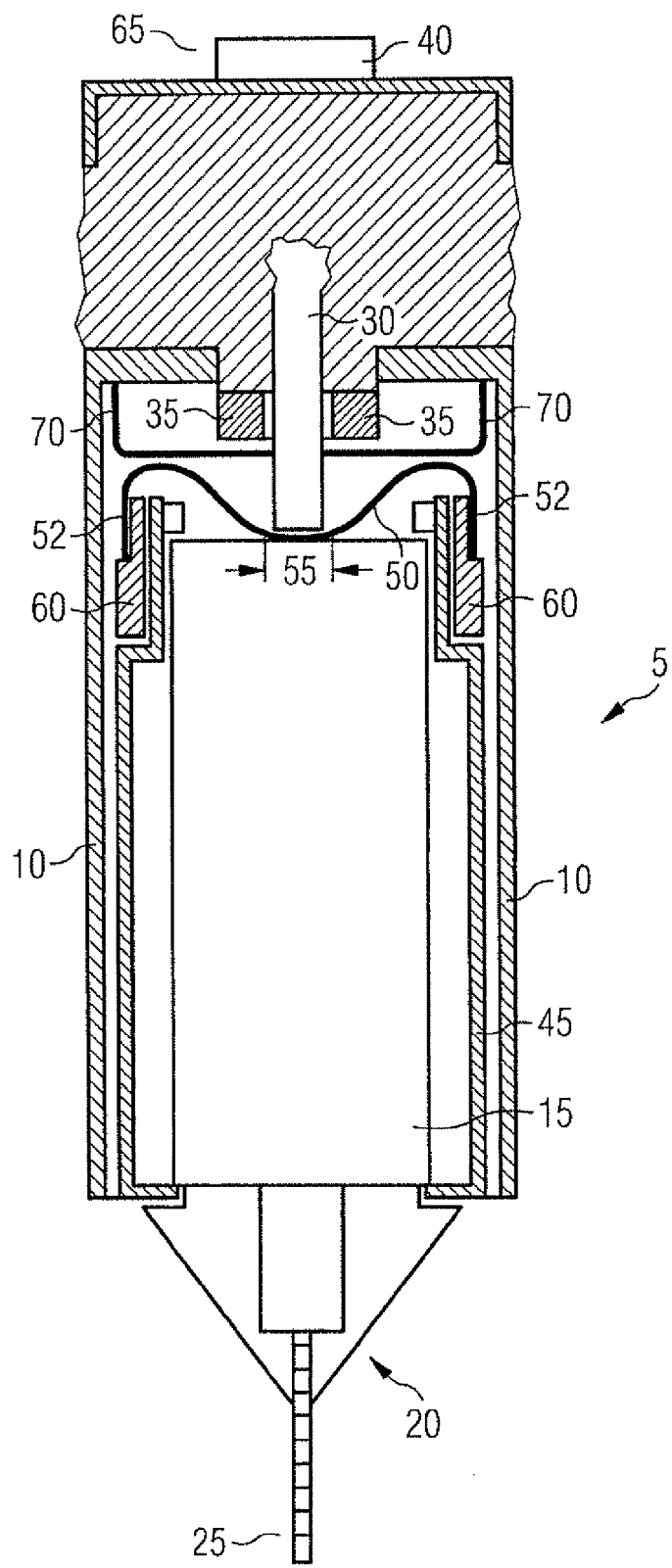
FIG. 1 schematically shows a simplified cross sectional side view of a drug delivery device according to an embodiment.

In FIG. 1 an embodiment of a drug delivery device 5 is shown, which is an injector for a liquid medication. The drug delivery device may be configured to deliver a plurality of, preferably user-settable, doses of a drug. The drug delivery device may be a pen-type device. The drug delivery device 5 comprises a housing 10, wherein a cartridge 15 containing a medical product (drug) is located. A needle unit 20 is located at the distal end 25 of the drug delivery device 5. Needle unit 20 may be secured against movement with respect to the housing. Through needle unit 20 the medical product can be injected into a patient.

It should be noted that the description of the drug delivery device 5 as shown in FIG. 1 is merely illustrative.

The drug delivery device as shown in FIG. 1 further comprises a cartridge retaining member 45 which is (releasably) secured to the housing 10. The cartridge retaining member 45 is adapted to retain the cartridge 15 within the drug delivery device 5. The cartridge retaining member 45 can be configured such that the cartridge 15 can be replaced by a user after it has been emptied.

Delivery of the medical product can be performed by means of a piston rod 30 or the like, which can be moved into the distal direction with respect to the cartridge 15. A piston (not explicitly shown) which is retained in the cartridge and seals the cartridge on the proximal end side may be moved in the distal direction with respect to the cartridge by the piston rod. Due to the moving piston, a dose of medical product may be delivered from the cartridge. Piston rod 30 may be threadedly engaged with a (lead screw) nut 35. During operation of the device, nut 35 is secured against rotational movement with respect to the housing 10 by lock nut 36 (cf. FIGS. 2 and 4) which may engage nut 35. Accordingly the piston rod may rotate and translate with respect to the housing when driven in the distal direction. Lock nut 36 and nut 35 may be held in engagement while cartridge retaining member 45 is secured to the housing 10. When the cartridge retaining member is released from the housing 10, nut 35 and lock nut 36 may disengage thereby allowing for rotation of the nut 35 with respect to housing 10. In order to reset the device, e.g. before securing a new and unused cartridge to the housing, piston rod 30 can then be screwed back into its initial position without such a movement being prevented due to engagement of nut 35 and lock nut 36. Thus, resetting of the device is facilitated.

Furthermore, the piston rod 30 is expediently connected to a drive mechanism (not explicitly shown), e.g. a mechanical or electrical drive mechanism, and to a dose setting mechanism (not explicitly shown). Drive mechanism and dose setting mechanism are configured to set a dose of the medical product and to move the piston in the distal direction such that the set dose is dispensed from the cartridge when a dispense button 40 of the drug delivery device is pressed.

When the cartridge 15 has been inserted into the cartridge retaining member 45 and the cartridge retaining member 45 has been secured to the housing, movement of the cartridge 15 in the distal direction is prevented by the cartridge retaining member 45. The cartridge 15 may abut the cartridge retaining member distally.

On the proximal side of the cartridge 15, a spring washer 50 is arranged within the housing 10. Spring washer 50 exerts a force on the cartridge 15 in the distal direction and secures the cartridge 15 against movement with respect to the cartridge retaining member 45 and against movement with respect to the housing 10. The loaded spring washer may hold the cartridge and the cartridge retaining member in permanent abutment on the distal end side of the cartridge 15. As shown in FIG. 1, the spring washer 50 is arranged in abutment with the cartridge 15 on the side of the cartridge which faces the proximal end 65 of the housing 10. Furthermore, the spring washer 50 comprises an opening 55 so as to allow the piston rod 30 to pass through spring washer 50 and to drive delivery of the medical product from the cartridge 15.

The spring washer 50 is fixed to the housing 10 in order to allow for the force to be exerted on the cartridge 15. In order to allow easy manufacturing of the drug delivery device 5, a (threaded) sleeve member 60 can be provided. The spring washer may be fixed to the sleeve member 60, e.g. by fixing elements 52 of the spring washer. The fixing elements 52 may extend in the axial direction. The spring washer may be fixed to the sleeve member 60 on an outer surface of the sleeve member. The sleeve member is fixed to the housing. Spring washer 50 may be fixed to sleeve member 60 by a snap-fit, for example. Sleeve member 60 and/or spring washer 50 is expediently secured against rotational and/or axial movement with respect to the housing. Of course, axial movement of the spring washer 50 for loading the spring washer or during relaxing of the spring washer is allowed. However, the region(s) in which the spring washer 50 is fixed to the housing 10, e.g. fixing elements 52, preferably do not rotate and/or do not move axially during operation of the drug delivery device.

The spring washer 50 may be provided with one, or a plurality of positioning elements. The respective positioning element may serve for keeping the spring washer 50 in a determined orientation, preferably in a predetermined angular orientation, with respect to the housing 10. For example, the fixing elements 52 may serve as positioning elements. The respective positioning element may cooperate with the housing or an element axially and rotationally locked to the housing for keeping the spring washer 50 in the predetermined orientation.

The respective positioning element/fixing element may be oriented axially. The respective positioning element/fixing element may extend from the outer circumference of the spring washer. Two positioning elements/fixing elements may be oppositely disposed. For example, the positioning elements/fixing elements may be arranged and/or axially guided within a respective guide slot 62a. The guide slot 62a may be axially and/or rotationally secured to the housing. The guide slot 62a may be axially limited, preferably distally and/or proximally, such that axial movement of the spring washer 50 with respect to the housing 10 may be restricted. The guide slot in cooperation with the positioning elements/fixing element which runs in the slot 62a may rotationally lock the spring washer 50 with respect to the housing 10.

Embodying a helical pressure spring to be rotationally locked with respect to a housing would be considerable more difficult than it is for a spring washer, as the helical spring is usually considerably deformed, in particular in the angular direction, under the influence of an external force. The spring washer may keep its shape in the angular direction even under the influence of considerable forces. Provision of a drug delivery device with accurately aligned parts is facilitated when applying a spring washer which is provided with according positioning elements/fixing elements.

The cartridge retaining member 45 can be secured to the housing 10 via a threaded connection provided between sleeve member 60 and cartridge retaining member 45. Sleeve member 60 is preferably provided with an inner thread for this purpose.

Exerting a force on the cartridge 15 in the distal direction can be performed by loading the spring washer 50 in the proximal direction when the cartridge retaining member 45 with the cartridge is mounted to the housing 10, e.g. by screwing the cartridge retainer into sleeve member. Thus, when the cartridge moves into abutment with the spring washer 50 and spring washer 50 is moved further in the proximal direction together with the cartridge, the spring washer is loaded and exerts a force on the cartridge in the distal direction.

The drug delivery device 5 of the embodiment depicted in FIG. 1 eliminates axial movement of cartridge 15 with respect to the housing 10 and with respect to the cartridge retaining member 45. This is for example advantageous when cartridges 15 with different lengths are used in the drug delivery device 5. It is, for example, possible to compensate for length differences, which may result from manufacturing tolerances between different cartridges or which may be the properties of different cartridge types, e.g. between 0.2 and 2 mm, by applying a spring washer. Consequently, during operation of the drug delivery device 5 axial movement of the cartridge 15 in the cartridge retaining member 45 is prevented and precision of drug delivery is improved.

It should be noted that different configurations of the spring washer 50 regarding its position within the housing 10 can be used for preventing axial movement of the cartridge. For example it is also possible to fix the spring washer 50 to the cartridge retaining member 45 or directly to the housing 10.

In order to ensure that the spring washer is kept in the range of elastic deformation, a further washer 70 can be arranged on the proximal side of the spring washer 50. The further washer 70 can be a disk washer or a spring washer having a higher strength as compared to the spring washer 50.

The further washer 70 limits the movement of the spring washer 50 such that the spring washer 50 is not plastically deformed. Thus, the geometry of the relaxed, i.e. unloaded, spring washer 50 and, in particular, its spring strength remain constant. As shown in FIG. 1, the further washer can be shaped like a disk. It is, however, also conceivable that the further washer has a curvature corresponding to the one of the spring washer 50.

The spring washer may contain metal or may be of metal. The respective spring washer may be made of steel, for example. The spring washer 50 preferably has a spring constant D which is smaller than the spring constant D of the further spring washer 70.

Preferably, the further washer 70 is secured against rotational movement with respect to the housing 10. The further washer does not have to be secured to the housing against axial movement. Rather, the spring washer 50 may limit distal movement of the further washer. An abutment element (not explicitly shown) may limit proximal movement of the further washer with respect to the housing. However, axial movement of the further washer 70 is expediently limited so as to allow the spring washer 50 to abut the further washer 70 and the further washer to abut the housing 10 before the spring washer is plastically deformed.

Figure 2:
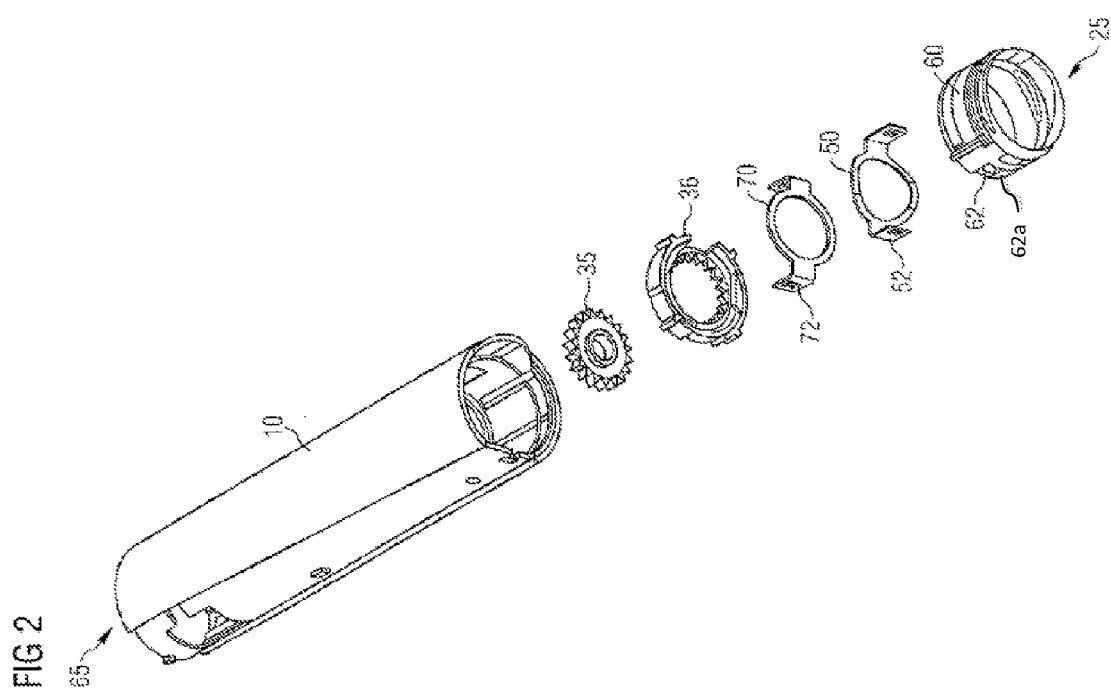
FIG. 2 schematically shows an exploded perspective view of a drug delivery device according to an embodiment.

The embodiment of FIG. 1 is now further explained with reference to FIG. 2. FIG. 2 is an exploded view of the drug delivery device 5 which shows several parts of the drug delivery device 5 in a side view before the parts are inserted into the housing 10. In FIG. 2, the (threaded) sleeve member 60 is shown which has holding means 62 for holding the spring washer 50. The spring washer 50 has two fixing elements 52, e.g. hook shaped, in order to fix the spring washer 50 to the sleeve member 60, for example by the respective fixing element 52 interacting with the respective holding means 62.

Furthermore, in FIG. 2 the (lead screw) nut 35 and the lock nut 36 are shown. The further washer 70 also includes fixing members 72, for securing the further washer against rotational and/or axial movement with respect to the housing 10. The elements shown in FIG. 2 fit into housing 10. The sleeve member 60 may be laser welded to housing 10, for example. As it is immediately apparent from FIG. 2, the spring washer 50 allows securing the cartridge 15 with respect to the housing 10 and within the cartridge retainer without requiring too much space. In particular, spring washer 50 is a lot more space saving than a helical coil spring of equal spring strength. Consequently a very compact drug delivery device 5 can be formed.

Figure 3:
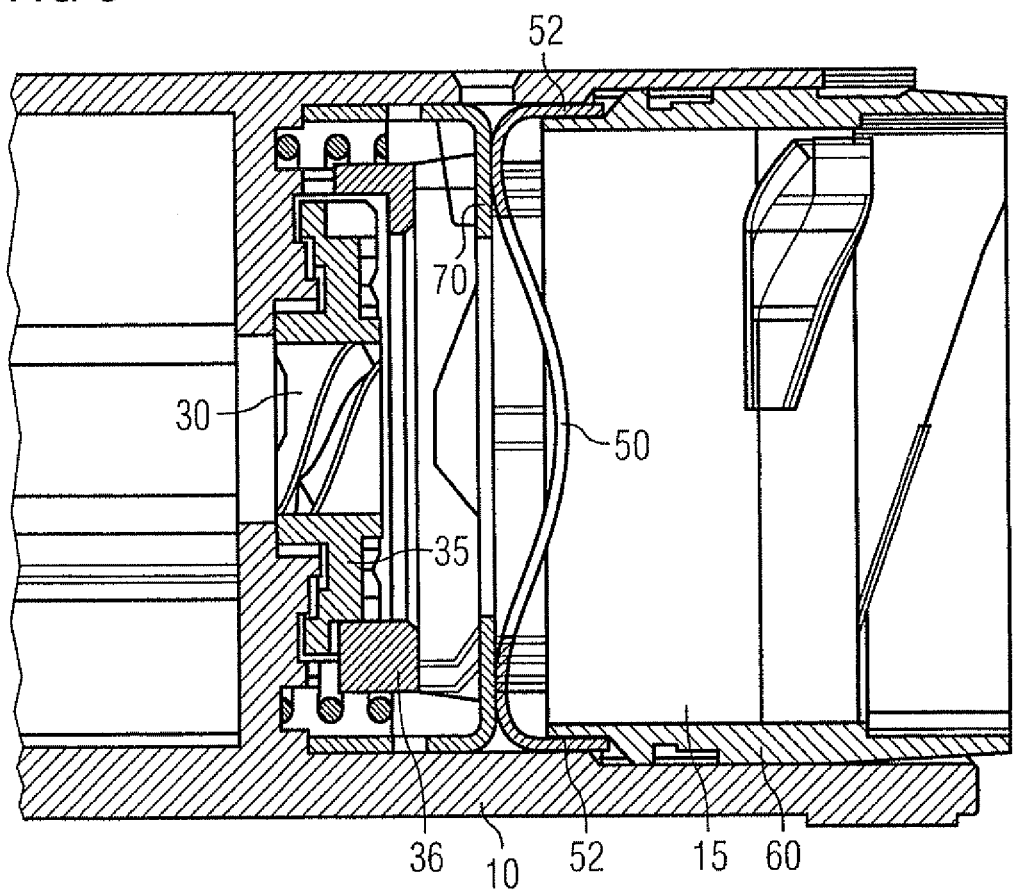
FIG. 3 schematically shows a detailed cross sectional side view of a part of a drug delivery device according to an embodiment.

With reference to FIG. 3 a further embodiment of the drug delivery device 5 is shown. FIG. 3 shows a detailed view of the spring washer 50 and the further washer 70. As shown in FIG. 3, the further washer 70 can be configured as a disk shaped washer.

Figure 4:
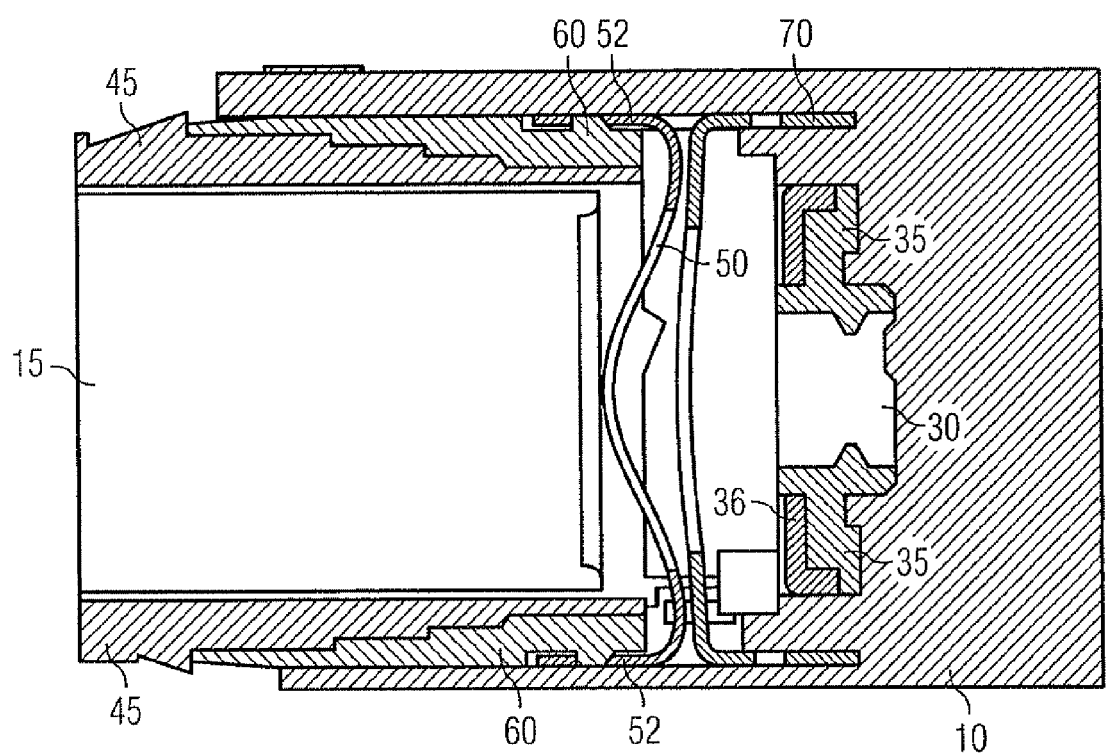
FIG. 4 schematically shows a detailed cross sectional side view of a part of a drug delivery device according to an embodiment.

Making now reference to FIG. 4 a further embodiment is shown. According to this embodiment the further washer 70 is also formed as a spring washer. The further washer 70 is curved in an axial and/or radial direction in a way that corresponds to or resembles the curvature of the spring washer 50.

Figure 5:
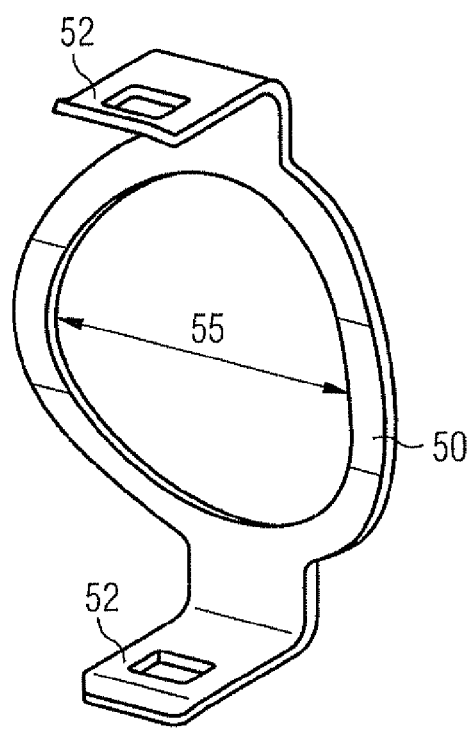
FIG. 5 schematically shows a side view of a spring washer according to an embodiment.

In FIG. 5 a detailed view of spring washer 50 is shown. The spring washer 50 is curved in axial and/or radial direction and includes fixing elements 52. Fixing elements 52 may be arranged oppositely with respect to one another. The spring washer can be a Belleville type spring washer.

Figure 6:
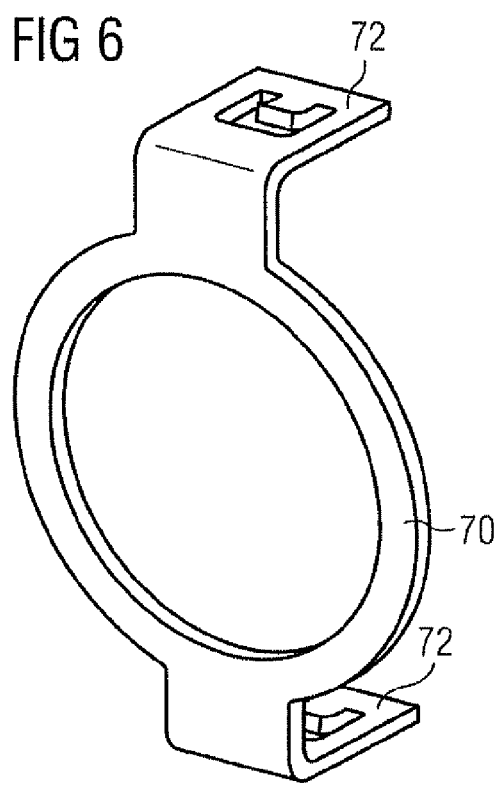
FIG. 6 schematically shows a side view of a further washer according to an embodiment.

Making now reference to FIG. 6 the further washer 70 is shown in more detail. The further washer 70 is provided as a disk like washer with fixing members 72 arranged on two opposite sides.

A method of manufacturing the drug delivery device 5 includes the steps of providing a housing with a proximal end and a distal end, providing a cartridge adapted to accommodate a drug, providing a cartridge retaining member adapted to retain the cartridge, arranging a spring washer within the housing and securing the cartridge retaining member to the housing, thereby loading the spring washer so as to exert a force on the cartridge and to secure the cartridge against displacement, in particular against axial displacement, with respect to the cartridge retaining member.

Other implementations are within the scope of the following claims. Elements of different implementations may be combined to form implementations not specifically described herein.

The invention claimed is:

1. A drug delivery device comprising:
a housing with a proximal end and a distal end,
a cartridge adapted to accommodate a drug,
a cartridge retaining member adapted to retain the cartridge, the cartridge retaining member releasably secured to the housing, characterized in that a first spring washer is arranged within the housing so as to exert a force on the cartridge and to secure the cartridge against movement with respect to the cartridge retaining member, the first spring washer having a proximal side being arranged so as to abut the cartridge on a side of the cartridge that faces the proximal end of the housing, and in that a second spring washer is arranged within the housing directly abutting the proximal side of the first spring washer and where a proximal side of the second spring washer abuts the housing to limit proximal movement of the second spring washer relative to the first spring washer in order to maintain abutment with the first spring washer.

2. The drug delivery device according to claim 1, wherein the first spring washer is biased so as to exert the force on the cartridge in the distal direction.

3. The drug delivery device according to claim 1, wherein the first spring washer is secured against axial movement with respect to the housing.

4. The drug delivery device according to claim 1, wherein the drug delivery device comprises a piston rod for dispensing a dose of the drug from the device when the piston rod is driven in the distal direction and wherein the first spring washer and the second spring washer each comprise an opening, the opening being arranged so as to allow the piston rod to run through the opening.

5. The drug delivery device according to claim 1, wherein the first spring washer is curved in axial and/or radial direction.

6. The drug delivery device according to claim 1, wherein the second spring washer is arranged to limit the loading distance of the first spring washer.

7. The drug delivery device according to claim 1, wherein the first spring washer is fixed to the housing.

8. The drug delivery device according to claim 1, wherein the first spring washer being fixed to the housing comprises the first spring washer fixed to a threaded sleeve member of the housing and the threaded sleeve member fixed to the housing.

9. The drug delivery device according to claim 1, wherein the first spring washer is fixed to a threaded sleeve member of the housing by fixing elements.

10. The drug delivery device according to claim 9, wherein the fixing elements comprise two oppositely disposed fixing elements which extend in the axial direction.

11. The drug delivery device according to claim 1, wherein the second spring washer having a higher strength as compared to the first spring washer.

12. The drug delivery device according to claim 11, wherein the second washer is arranged to limit deformation of the first spring washer to elastic deformation.

13. The drug delivery device according to claim 11, wherein the second washer is curved in an axial and/or a radial direction so as to correspond to a curvature of the first spring washer.

14. The drug delivery device according to claim 1, wherein the first spring washer is provided with one or a plurality of positioning elements, which keep the first spring washer in a determined orientation.

15. The drug delivery device according to claim 14, further comprising a guide slot axially and/or rotationally secured to the housing, wherein each positioning element is arranged and/or axially guided within the respective guide slot.

16. The drug delivery device according to claim 14, wherein the plurality of positioning elements comprise two oppositely disposed positioning elements,
wherein the determined orientation comprises a predetermined angular orientation with respect to the housing, and
wherein the positioning elements extend from the outer circumference of the first spring washer.

17. A method of manufacturing a drug delivery device comprising:
providing a housing with a proximal end and a distal end,
providing a cartridge adapted to accommodate a drug,
providing a cartridge retaining member adapted to retain the cartridge and be releasably secured to the housing,
arranging a first spring washer having a proximal side within the housing, characterized in that the cartridge retaining member is releasably secured to the housing, thereby loading the first spring washer and a second spring washer so as to exert a force on the cartridge and to secure the cartridge against displacement with respect to the cartridge retaining member, the first spring washer being arranged so as to abut the cartridge on a side of the cartridge that faces the proximal end of the housing, and the second spring washer being arranged within the housing directly abutting the proximal side of the first spring washer and where a proximal side of the second spring washer abuts the housing to limit proximal movement of the second spring washer relative to the first spring washer in order to maintain abutment with the first spring washer.

18. A method of using a first spring washer and a second spring washer to secure a cartridge which contains a drug in a cartridge retaining member releasably attached to a housing of a drug delivery device against displacement with respect to the cartridge retaining member, the first spring washer having a proximal side being arranged so as to abut the cartridge on a side of the cartridge that faces the proximal end of a housing of the drug delivery device, and the second spring washer being arranged within the housing directly abutting the proximal side of the first spring washer and where a proximal side of the second spring washer abuts the housing to limit proximal movement of the second spring washer relative to the first spring washer in order to maintain abutment with the first spring washer.

* * * * *